(12) United States Patent
Fiedler et al.

(10) Patent No.: US 10,398,456 B2
(45) Date of Patent: Sep. 3, 2019

(54) ORTHOPEDIC SURGICAL PLIERS-LIKE TOOL FOR HOLDING AND GRIPPING A PATELLA BONE

(71) Applicant: LIMA CORPORATE S.P.A., San Daniele del Friuli (IT)

(72) Inventors: Christoph Fiedler, Diekhof (DE); Massimo Ceconi, Travesio (IT)

(73) Assignee: Lima Corporate S.P.A., San Daniele del Friuli (UD) (IT)

( * ) Notice: Subject to any disclaimer, the term of this patent is extended or adjusted under 35 U.S.C. 154(b) by 204 days.

(21) Appl. No.: 15/647,897

(22) Filed: Jul. 12, 2017

(65) Prior Publication Data
US 2018/0014839 A1    Jan. 18, 2018

(30) Foreign Application Priority Data
Jul. 14, 2016   (EP) ..................... 16179380

(51) Int. Cl.
*A61F 2/46*       (2006.01)
*A61B 17/88*      (2006.01)
*A61B 17/17*      (2006.01)
*A61B 17/16*      (2006.01)

(52) U.S. Cl.
CPC ...... *A61B 17/1767* (2013.01); *A61B 17/1611* (2013.01); *A61B 17/8866* (2013.01); *A61F 2/461* (2013.01); *A61B 17/1677* (2013.01); *A61F 2002/4622* (2013.01); *A61F 2002/4623* (2013.01)

(58) Field of Classification Search
CPC ............ A61B 17/1767; A61B 17/8866; A61B 17/1611; A61F 2002/4622; A61F 2/461

USPC .......................................................... 81/300
See application file for complete search history.

(56) References Cited

U.S. PATENT DOCUMENTS 4,997,432 A * 3/1991  Keller ................. A61B 17/025
                                              600/219
5,536,271 A   7/1996  Daly et al.
5,944,723 A * 8/1999  Colleran ............ A61B 17/8866
                                              606/208

(Continued)

*Primary Examiner* — David W Bates
(74) *Attorney, Agent, or Firm* — Hickman Palermo Becker Bingham LLP; Malgorzata A. Kulczycka (57) ABSTRACT

The present invention relates to an orthopedic surgical pliers-like tool (1) for performing surgery on the patella bone, comprising: —at least a couple of jaws (2, 3) coupled to corresponding handle members (12, 13) pivotally mounted with a hinge bolt (5) in relation with one another; —a distal clamp portions (8, 9) on each jaw (2, 3) for gripping and holding at least the periphery of a patella bone; —an intermediate force transmission mechanism (4) between the tool handle members (12, 13) and the jaws (2, 3); —a couple of arms (20, 30) in said intermediate force transmission mechanism (4) structurally independent from the handle members (12, 13) and interposed between the handle members (12, 13) and the jaws (2, 3); —an elastic member (25, 35) in each arm (20, 30) for coupling each arm to a corresponding handle member (12, 13) in a first linking point (38, 39); —a second more distal linking point (31, 33) in each arm (20, 30) engaging a corresponding distal end (43, 42) of a handle member (12,13); —the first linking point (38, 39) of one arm (20, 30) and the second linking point (31, 33) of the other arm being cross linked to the same handle member (12, 13).

20 Claims, 11 Drawing Sheets

(56) References Cited

U.S. PATENT DOCUMENTS

| | | | |
|---|---|---|---|
| 5,968,051 A * | 10/1999 | Luckman | A61B 17/8802 |
| | | | 606/86 R |
| D667,552 S | 9/2012 | Claypool et al. | |
| 8,728,087 B2 * | 5/2014 | Soliman | A61B 17/158 |
| | | | 269/3 |
| 2006/0142777 A1 | 6/2006 | Bastian | |
| 2008/0177394 A1 | 7/2008 | Chauhan | |
| 2013/0338672 A1 * | 12/2013 | Harris | A61B 17/1767 |
| | | | 606/88 |
| 2016/0278794 A1 * | 9/2016 | Boldt | A61F 2/3877 |
| 2019/0029699 A1 * | 1/2019 | Wallace | A61F 2/4684 |

* cited by examiner

ORTHOPEDIC SURGICAL PLIERS-LIKE TOOL FOR HOLDING AND GRIPPING A PATELLA BONE

BENEFIT CLAIM

This application claims the benefit under 35 U.S.C. § 119 of European Patent Office application 16179830.7, filed Jul. 14, 2016, the entire contents of which are hereby incorporated by reference for all purposes as if fully set forth herein.

FIELD OF THE INVENTION

The present invention relates to an orthopedic surgical tool for holding a human patella bone and providing a guide so that a predetermined portion of the patella may be accurately removed by sawing.

More specifically, the invention relates to a pliers-like tool or device for performing surgery on the patella, commonly known as the knee cap. Specifically, the tool is a clamp for holding the patella while removing the damaged articulating surface and replacement thereof with a prosthesis, also known as a patella button.

KNOWN ART

As it is well known in this specific technical field, the patella is a sesamoid of lens shaped bone which slides in a groove between the condyles of the femur. Its function is to increase the efficiency of the quadriceps muscle by shifting the line of action of the muscle's pull forward.

As the knee articulates, the muscles and tendons force the patella toward the condyles of the femur. Consequently, there is considerable relative motion between the patella and the other bones comprising the knee joint.

Because of aging, disease or sporting activities, the articulating surfaces of the knee may degrade. To treat certain pathologies, it has become common to surgically remove the condyles and replace these structures with prosthetic implants. By the same processes, the articulating surfaces of the patella may also be replaced. Because of the tendons connected to the patella, it is generally advisable to replace only the articulating surface. A patella button made for instance by polyethylene with an articulating surface, with or without a metal base plate, has been used to replace the posterior or interior side of the patella, adjacent the femoral condyles. To implant such a prosthesis, the posterior surface of the patella is resected to produce a flat surface upon which the prosthesis can be mounted.

The process of cutting, drilling and replacing the damaged surface of a patella is complex and time consuming. In the past, the surgeon has often relied on his skill of hand and eye in manipulating a sagittal saw to make an appropriate cut. Nowadays, the process requires three separate basic steps:
1) Resecting or removing the damaged posterior articulating surface of the patella;
2) providing means in the resected patella for receiving the prosthesis; and
3) attaching the prosthesis to the resected and prepared patella.

To accomplish these three steps, several separate devices are employed. These include a device for firmly holding the patella to expose its posterior surface; a saw; a saw guide to control the portion of the patella that is to be removed; a drill to provide means to attach the implant securely; a drill guide to control the placement and depth of the means for attaching the prosthetic implant; and a device to insert the prosthesis and press the prosthesis into place. This latter device ensures that the attachment of the prosthesis with the resectioned patella is secure.

Devices for such a process have been developed and described. In particular, clamp-like patella resection and replacement devices have been described in U.S. Pat. Nos. 5,147,365 and 6,010,509.

The U.S. Pat. No. 5,147,365 disclosed a pliers-like device for clamping and guiding a sagittal saw for the resection of a pre-determined portion of the patella. A rotating, calibrated stylus measures the position of the patella with respect to the integral sagittal saw. Capture slots are provided in each of the jaw members through which the sagittal saw may be mounted. The stylus and a draw bar served as a saw guide. The stylus and draw bar assembly comprised a scale bushing which fits through bores provided at the fulcrum of the clamp. The stylus arm carried a scale post, which could be adjusted vertically. This enables the surgeon to determine the precise amount of the patella, which is to be removed.

U.S. Pat. No. 6,010,509 disclosed a patella resection and replacement device comprising a pliers-like clamp for gripping and holding the patella, the clamp having a spring biased hinge bolt. A specially designed drill guide may be snapped into place and removed from the hinge bolt without releasing the patella during surgery. Similarly, a specially designed patella button presser may be snapped into place and removed from the hinge bolt. Without the necessity of releasing, re-gripping and re-orienting the patella during the process, the time for the operation is greatly reduced.

While being advantageous under many point of views the above tools still have some limitations. In fact, the problems encountered in connection with the use of existing tools, generally known as "patella clamps", are several.

The clamp tool is used to securely hold the patella during surgery. Most of the existing patella clamps are rather large and bulky. When in use, the tool blocks the surgeon's view and prevents physical access to the joint.

Moreover, some of the existing patella presser clamps are provided with rather long handles to improve the mechanical advantage. However, this increases the risks of fracturing the patella during the operation, a very undesirable occurrence.

The technical problem underlining the present invention is that of providing a new orthopedic surgical pliers-like tool for performing surgery on the patella bone having structural and functional features to overcome the limits of the known pliers-like tools and to allow handling softly the patella bone while ensuring a stable gripping.

Another aim of the present invention is to provide a tool for the replacement of a patella which is simpler, less cumbersome, easier to use and does not block the surgeon's view during the operation.

It is a further objective of the present invention to provide a pliers-like device capable to provide a regulated force to the gripping clamps of the tool while ensuring a firm and stable positioning of the gripping clamps holding the patella bone.

SUMMARY OF THE INVENTION

The inventive idea at the basis of the present invention is that of providing a sort of intermediate force transmission system between the tool handles used by the surgeon and the gripping clamps for holding the patella bone; such an intermediate force transmission system including resilient and elastic means for exerting a gentle elastic extra force when the tool has gripped the patella bone.

According to this inventive idea, the technical problem is solved by an orthopedic surgical pliers-like tool for holding and gripping a patella bone comprising:

- at least a couple of jaws coupled to corresponding handle members pivotally mounted with a hinge bolt in relation with one another;
- a distal clamp portions on each jaw for gripping and holding at least the periphery of a patella bone;
- an intermediate force transmission mechanism between the tool handle members and the jaws;
- a couple of arms in said intermediate force transmission mechanism structurally independent from the handle members and interposed between these handle members and the jaws;
- an elastic member in each arm for coupling each arm to a corresponding handle member in a first linking point;
- a second more distal linking point in each arm engaging a corresponding distal end of a handle member;
- the first linking point of one arm and the second linking point of the other arm being cross linked to the same handle member.

It should be noted each of the arms is structured to be pre-inclined in an unloaded condition and to be kept substantially parallel to the other arm in the fully loaded condition so to optimize the load transfer to the patella bone.

Each of said arms is substantially flat and has an arched shape with a distal end coupled to a corresponding jaw and a proximal end overlapping the handle members more proximally with reference to the hinge bolt.

Advantageously, said second more distal linking point is located in a slot formed in each of the arms and engaged by a corresponding sliding pin fixed perpendicularly to the distal end of each handle member.

Moreover, each of the arm includes an elastic member for coupling each arm to the corresponding handle member and each elastic member comprises an opening in each of the arms wherein an elastic element or tongue is protruding inside the opening.

The tongue is a sort of leaf spring having one end fixed to the arm structure and the other end free to move inside the respective opening, said enlarged free end of the elastic element is linked to a first link point of the handle member by a corresponding pin.

In other words, each handle member is cross linked to said enlarged free end of the elastic element of one arm by a pin located in an intermediate position of the handle member and to the other arm by a sliding pin located at the distal end of the handle member and sliding inside a slot of the other arm. The sliding pin is fixed perpendicularly to the distal end of each handle member.

In the pliers-like tool according to the invention the jaws are mounted in a removable manner on the corresponding distal end of said arms with interposition of an elastic element.

A guide slot is provided at the distal end of each arm for hosting a corresponding pin formed integrally with the corresponding jaw and extended in a direction perpendicular to the longitudinal extension of the jaws. Each of said pin is free to slide inside the corresponding guide slot to provide a slight axial movement of each jaw on the respective arm in contrast with said elastic element.

When a second or further elastic gripping action is demanded by the manual pressure of the handle members the compression springs will intervene allowing the pins to slide inside the relative slots.

It should be further noted that a locking means is provided at the arms' proximal ends, to maintain a desired distance between the distal clamp portions of the jaws or jaws.

Such a locking means includes a saw-toothed bar that is pivotally mounted on a hinge at the proximal end of one arm and is engaged by a ratchet provided on the proximal end of the other arm when the arms are forced to approach one toward the other by the handle members.

A selected embodiment will now be explained with reference to the drawings. It will be apparent to those skilled in the orthopedic field from this disclosure that the following descriptions of the embodiment is provided for illustration only and not for the purpose of limiting the invention as defined by the appended claims and their equivalents.

DETAILED DESCRIPTION

With reference to the enclosed drawings figures, with 1 it is globally and schematically shown an orthopedic surgical pliers-like tool for performing surgery on the patella bone.

The tool 1 of the present invention is a pliers-like clamp having a pair of combination prongs or jaws 2, 3 and corresponding handle members 12, 13 pivotally mounted with a hinge bolt 5 in relation with one another.

Figure 4:
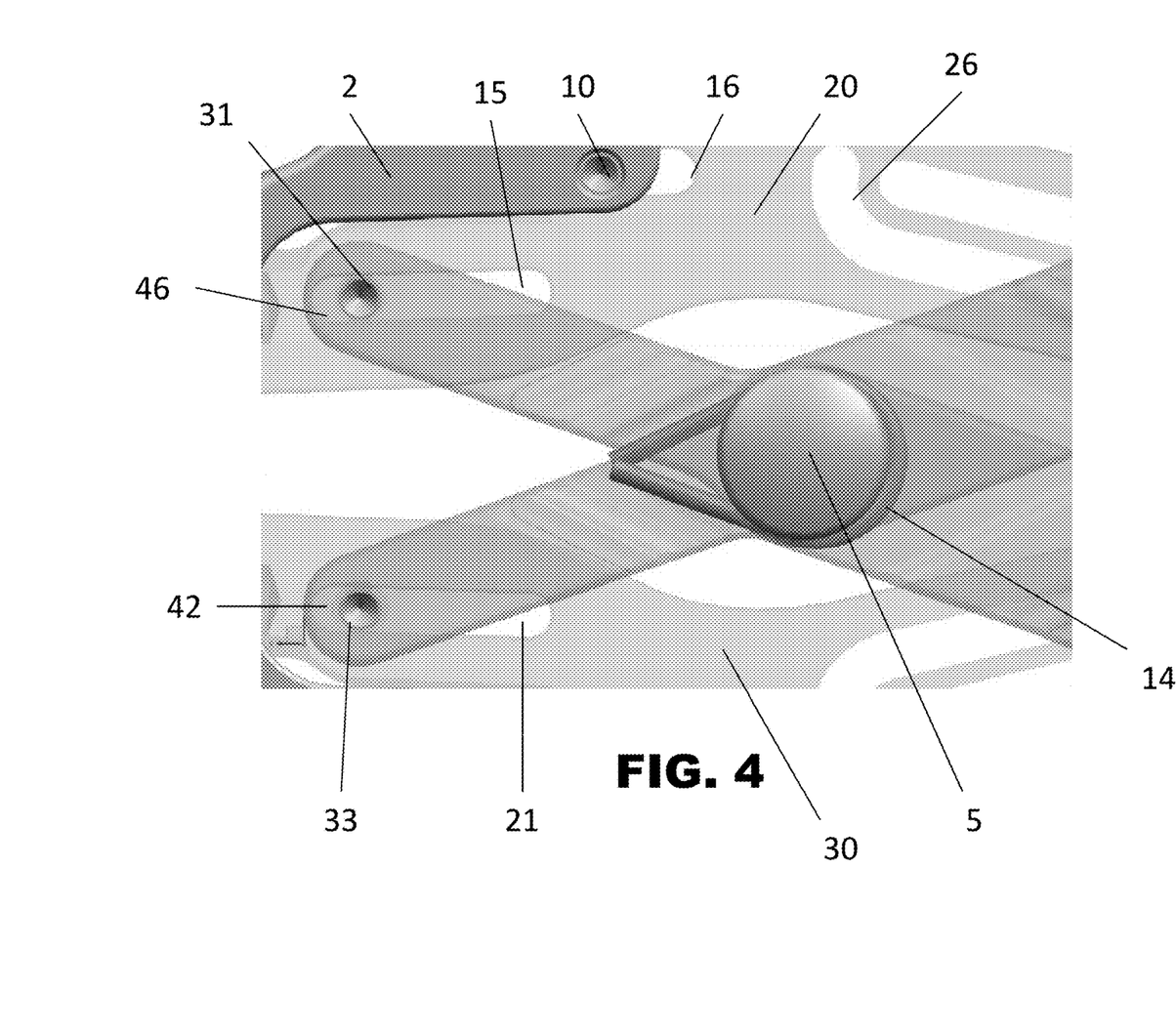
FIG. 4 shows another enlarged scale front view of another particular of the pliers-tool according to the invention.

The tool 1 is normally held in an open or ready to use position by the hinge bolt 5, which is preferably elastically biased by a spring 14 as shown in the more detailed view of FIG. 4.

The spring 14 exerts its elastic biasing force in order to keep open the jaws 2 and 3 when the tool 1 in the ready to use position.

The jaws 2, 3 have corresponding distal clamp portions 8 and 9 both having a relative flat clamping surface 18, 19 for gripping and holding the periphery of a patella bone (not shown in the figures).

Figure 1:
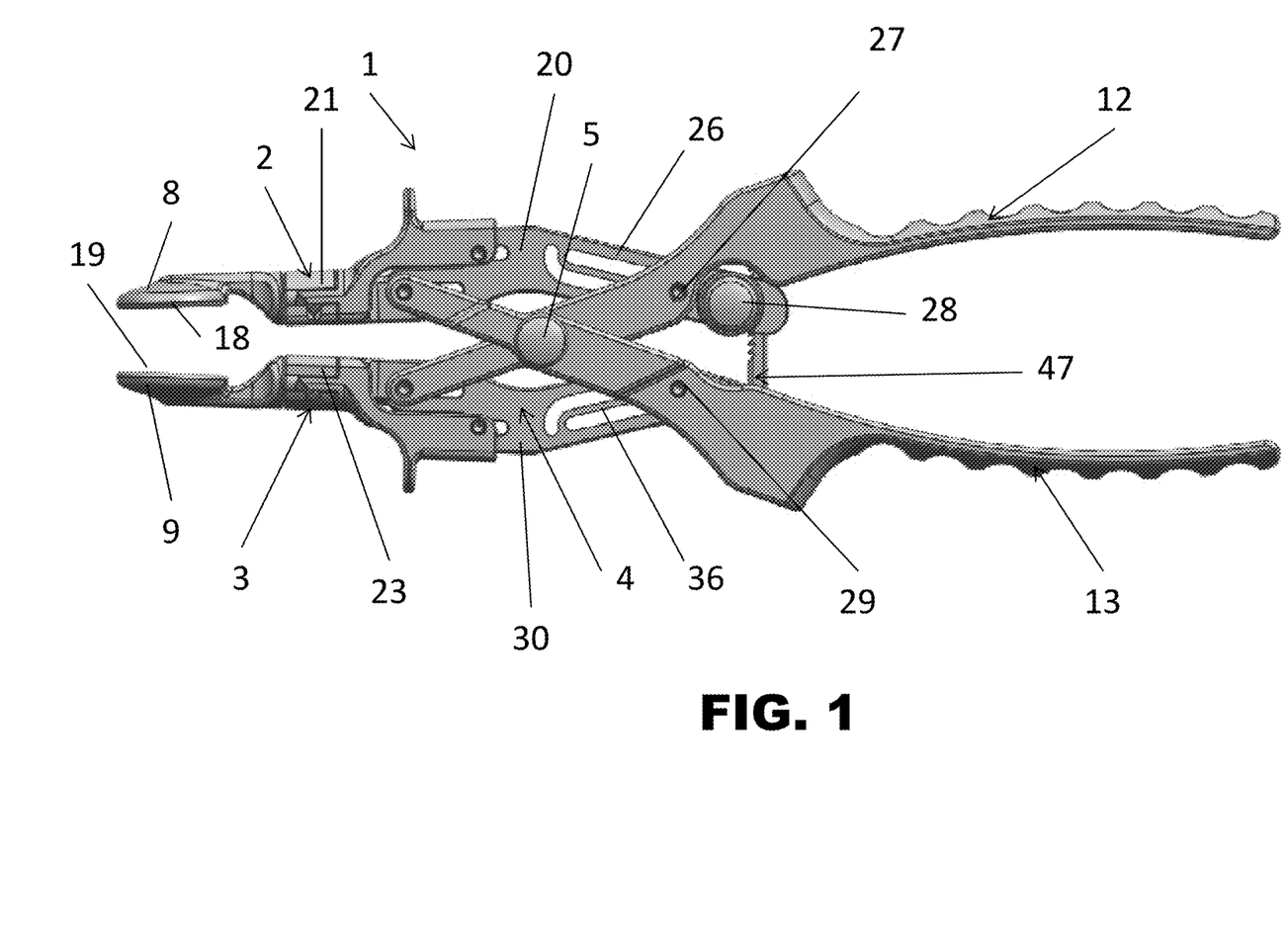
FIG. 1 shows a schematic and top view of an orthopedic surgical pliers-like tool realized according to the present invention in a ready to use position.

These flat clamping surfaces 18 and 19 of the corresponding distal ends 8, 9 of the jaws 2, 3 are faced one another and ready to be driven in reciprocal approaching vicinity when the tool 1 is in the ready to use position shown in FIG. 1. A predetermined clearance is set between the surfaces 18 and 19 when the tool 1 is in the ready to use position.

Differently from the known solutions, the pliers-like tool 1 of the present invention include an intermediate force transmission system 4 or mechanism between the tool handles 12, 13, used by the surgeon, and the jaws 2, 3.

This intermediate force transmission system 4 comprises a couple of arms 20 and 30 which are structurally independent from the handle members 12, 13 and are interposed between these handle members 12, 13 and the jaws 2, 3.

More particularly, each of the arms 20, 30 is substantially flat and has an arched shape with a distal end 22, 32 coupled to a corresponding jaw 2, 3 and a proximal end 24, 34 overlapping the handle members 12, 13 more proximally with reference to the hinge bolt 5.

The two arms 20, 30 are substantially symmetrical in shave with the only exemption of the proximal end 24, 34 that is shaped differently for hosting different elements of the tool 1 that will be explained hereinafter.

The jaws 2, 3 are mounted each in a removable manner on the corresponding distal end 22, 32 of the arms 20, 30 with interposition of an elastic element 45, 55 that will be disclosed hereinafter.

In this respect, a guide slot 16, 17 is provided on each arm 20, 30 for hosting a corresponding pin 10, 11 formed integrally with the corresponding jaw 2, 3 and extended in a direction perpendicular to the longitudinal extension of the jaws. Each pin 10, 11 is free to slide inside the guide slot 16, 17 to provide a slight axial movement of each jaw 2, 3 on the respective arm 20, 30.

Figure 2:
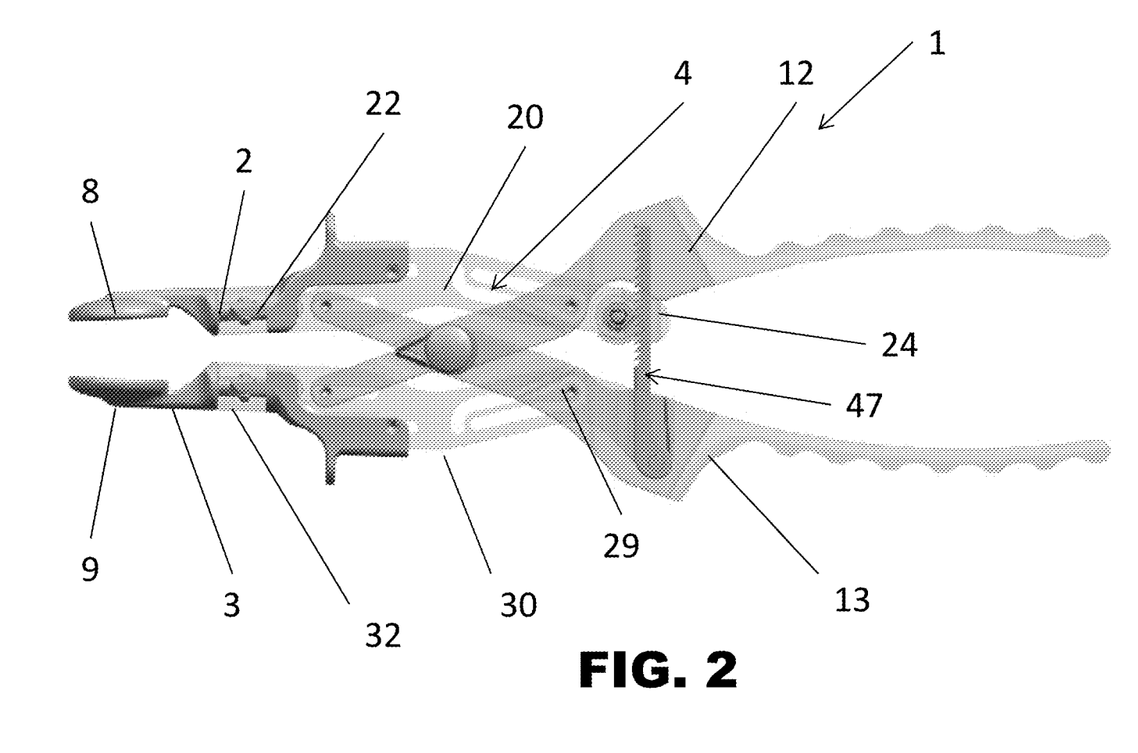
FIG. 2 shows a schematic view of the pliers-like tool of FIG. 1 with some elements shown in transparency.
Figure 3:
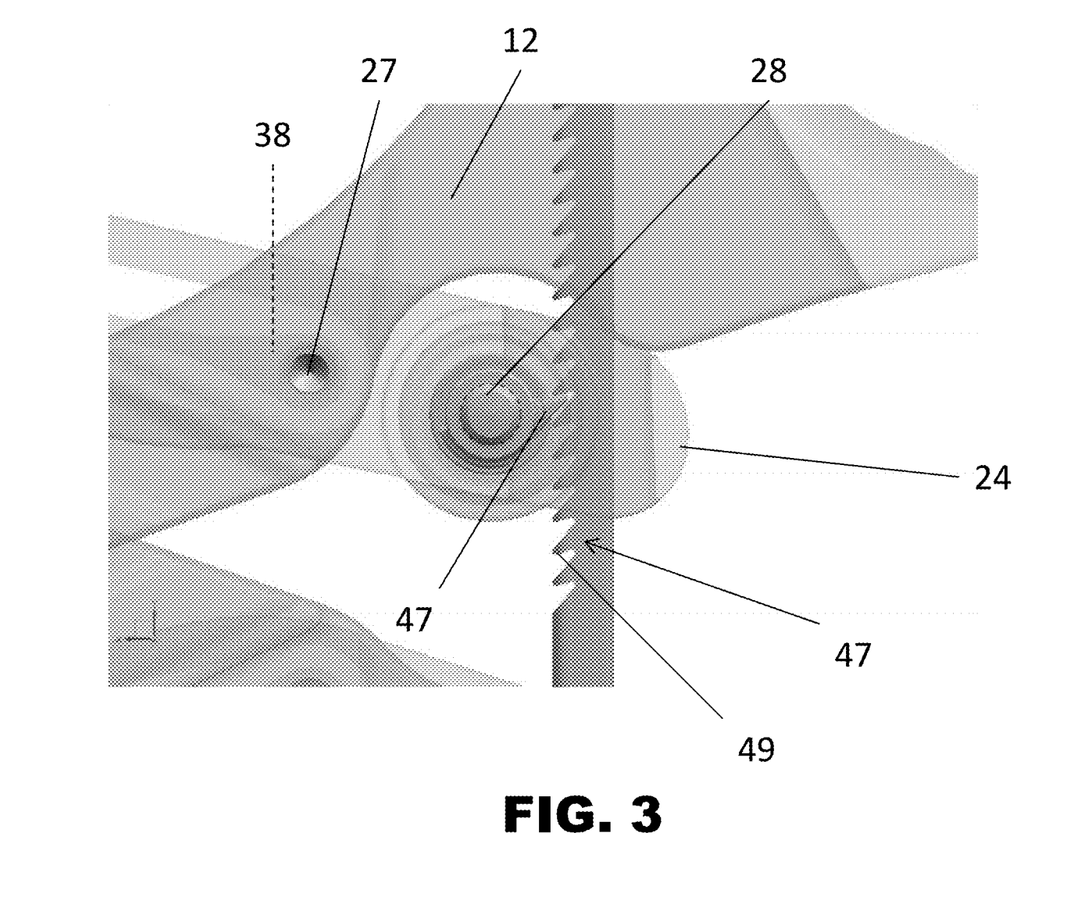
FIG. 3 shows an enlarged scale front view of a particular of the pliers-tool according to the invention.

The distal clamp portions 8, 9 of the jaws 2, 3 are removable and are supported by a corresponding pin that is supported in a seat provided at the distal end of each arm 20, 30 and is partially visible in FIG. 2. A fastener mechanism 21, 23 is provided on each jaw to quick release the distal clamp portions 8, 9 for possible cleaning or substitution with other shaped clamps.

Both the arms 20 and 30 include connecting means for coupling the orthopedic surgical pliers-like tool of the present invention with other associated and cooperating tools such as, for instance, a drill guide or a resection guide not shown in the drawings. The invention is not focused on the connecting means with such optional tools but it's important to remark that the arms are provided with those means.

Advantageously, according to the invention, each of the arm 20, 30 includes an elastic member 25, 35 for coupling each arm 20, 30 to the corresponding handle member 12, 13.

The elastic members 25, 35 include respective portions of the arm, which are configured as resilient members which return to their original form or position after being bent by an acting force.

The elastic members 25, 35 provide portions having elasticity and resilience which is greater compared to the overall elasticity and resilience of the arms 20, 30.

Each elastic member 25, 35 comprises an opening 26, 36 in each of the arms 20, 30 wherein an elastic element 6, 7 or tongue is protruding inside the opening.

This tongue may be considered a sort of leaf spring having one end fixed to the arm structure and the other end free to move inside the respective opening 26 or 36.

Each one of these elastic elements 6, 7 or tongue has one end formed integrally with the arm 20, 30 and an opposite enlarged free end 38, 39 that has a two-dimensional shape substantially similar to a drop.

The enlarged free end 38 or 39 of the elastic element 6 or 7 is linked to a first point of the handle member 12 or 13 by a corresponding pin 27, 29.

This is a first contact or linking point between the handle member and the arm.

More specifically, each handle member 12, 13 of the pliers-like tool 1 of the present invention is coupled to the intermediate force transmission system 4 in a couple of linking points.

A first link point is the enlarged free end 38 or 39 of elastic element 6, 7 or tongue of one arm 20, 30.

A second linking point is located in a slot 15, 31 formed in each of the arms 20, 30 which is engaged by a corresponding sliding pin 31, 33 fixed perpendicularly to the distal end 42, 46 of each handle member 12,13.

The slots 15 and 31 are substantially parallel to the shorter slots 16 and 17 provided in a slightly staggered position on the corresponding arms 20, 30.

Therefore, in view of the above description it should be evident that the handle member 12 is cross linked to the enlarged free end 38 of the elastic element 6 of the arm 20 by the pin 27 located in an intermediate position of the handle member 12, more proximal than the hinge 5, and by the pin 33 located at the distal end 42 and sliding inside the slot 21 of the other arm 30.

In a corresponding manner, the handle member 13 is cross linked to the enlarged free end 39 of the elastic element 7 of the arm 30 by the pin 29 located in an intermediate position of the handle member 13, more proximal than the hinge 5, and by the pin 31 located at the distal end 46 and sliding inside the slot 15 of the other arm 20.

It should be noted that one handle member 12 is linked to the arm 20 in a first link point 38 and to the other arm 30 in a second link point represented by the sliding coupling between the pin 33 and the slot 21.

Accordingly, the other handle member 13 is linked to the second arm 30 in a first link point 39 and to the first arm 20 in a second link point represented by the sliding coupling between the pin 31 and the slot 15.

Keeping in mind that the two handle members 12, 13 are coupled in the hinge bolt 5, the above construction represent an intermediate force transmission system or mechanism that allows a first gentle exertion of gripping force when the surgeon acts of the handle members to grip and hold the patella bone through the distal approaching clamp portion 8 and 9.

However, according to the invention, a second or further elastic gripping action may be exerted by the pliers-like tool 1 of the present invention according to the further features included in the tool 1 and disclosed hereinafter.

Figure 5:
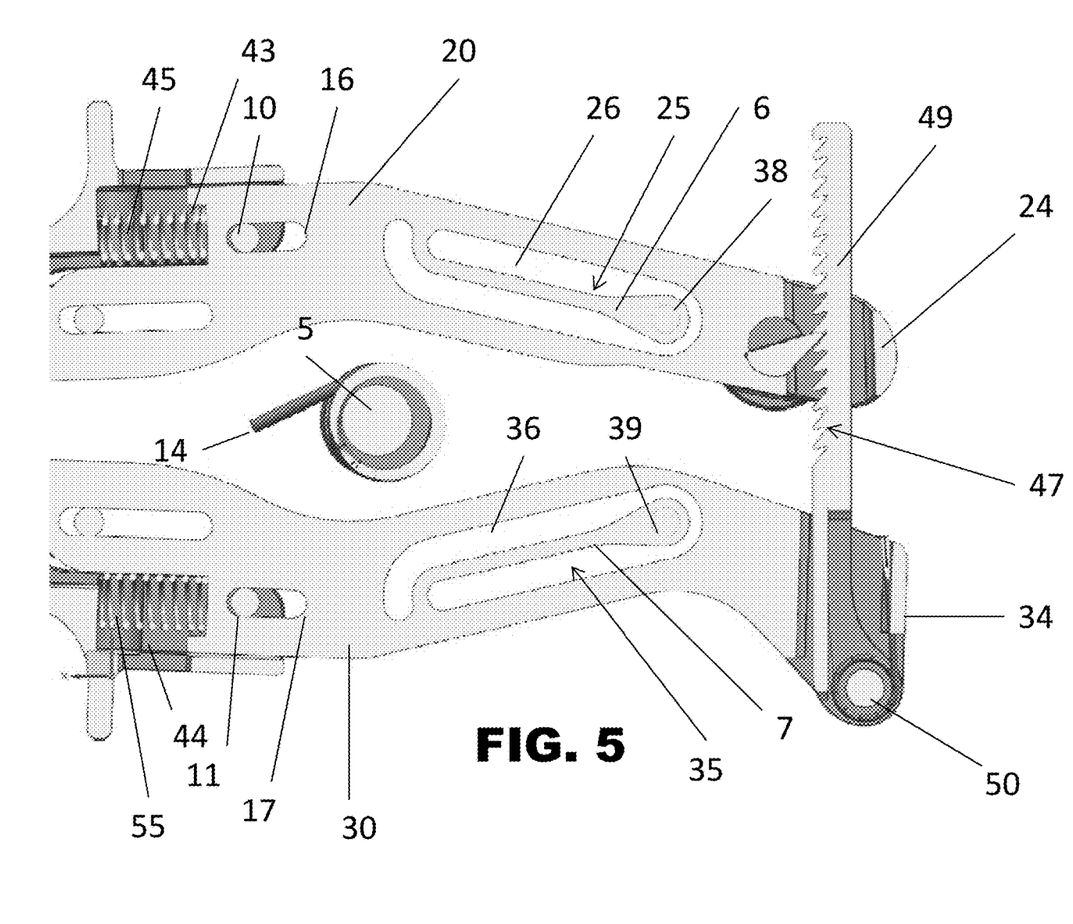
FIG. 5, FIG. 6, FIG. 7, FIG. 8, FIG. 9 show different schematic top views of an intermediate force transmission system incorporated into the pliers-like took of the invention and shown in different functioning phases.

As may be seen in FIG. 5 and following, a compression spring 45 or 55 is provided between each one of the arms 20 or 30 and the corresponding jaws 2, 3.

The compression spring 45 or 55 is located in a corresponding seat 43, 44 formed between the arm 20, 30 and the corresponding jaws 2, 3 in the proximity of the slot 16 or 17.

We may say that the seats 43 and 44 are substantially aligned with the corresponding adjacent slots 16 and 17.

When a second or further elastic gripping action is demanded by the manual pressure of the handle members 12,13, the compression springs 45, 55 will intervene allowing the pins 10 and 11 to slide inside the relative slots 16, 17.

It must be noted that a locking means 47 is provided at the arms proximal ends 24, 34 to maintain a desired distance between the distal ends 8, 9 of the jaws or jaws 2,3. An example of the locking means is a saw-toothed bar 49 that is pivotally mounted on a hinge 50 at the proximal end 34 of the arm 30, as shown in FIGS. 5-9.

The shape of the proximal end 34 of the second arm 30 is different from the shape of the other proximal end 24 of the first arm 20 just to host the hinge 50.

A tooth or ratchet 47 is provided on the proximal end 24 of the first arm 20 to engage step by step the teeth of the saw-toothed bar 49 when the arms 20, 30 are forced to approach one toward the other.

A pushing button 28 is provided to release the ratchet 47 from its engagement with the teeth of the saw-toothed bar 49 and release the handle members 12,123 to return the tool 1 in the ready to use position.

Let's now see the functioning of the pliers-like tool 1 of the present invention.

The pressure action applied by the surgeon on the handle members 12, 13 allows closing the two handle members one toward the other. This pressure action pushes both arms 20, 30 to get closer.

This pressure action is obtained against the elastic force of the torsion spring 14 of the hinge bolt 5 that in the ready to use position tends to keep the handle members open and, as a consequence, the arms 20, 30 in their rest position one distant from the other.

The handle members 12, 13 can be closed freely by the surgeon until the distance between the flat surfaces 18, 19 of the jaws will reach a minimum clearance corresponding substantially to the patella bone thickness.

Thanks to the pressure action applied on the handle members 12, 13 the arms 20 and 30 that are connected to the handle members are forced to get closer with their respective proximal ends 24, 24 approaching one toward the other.

Figure 6:
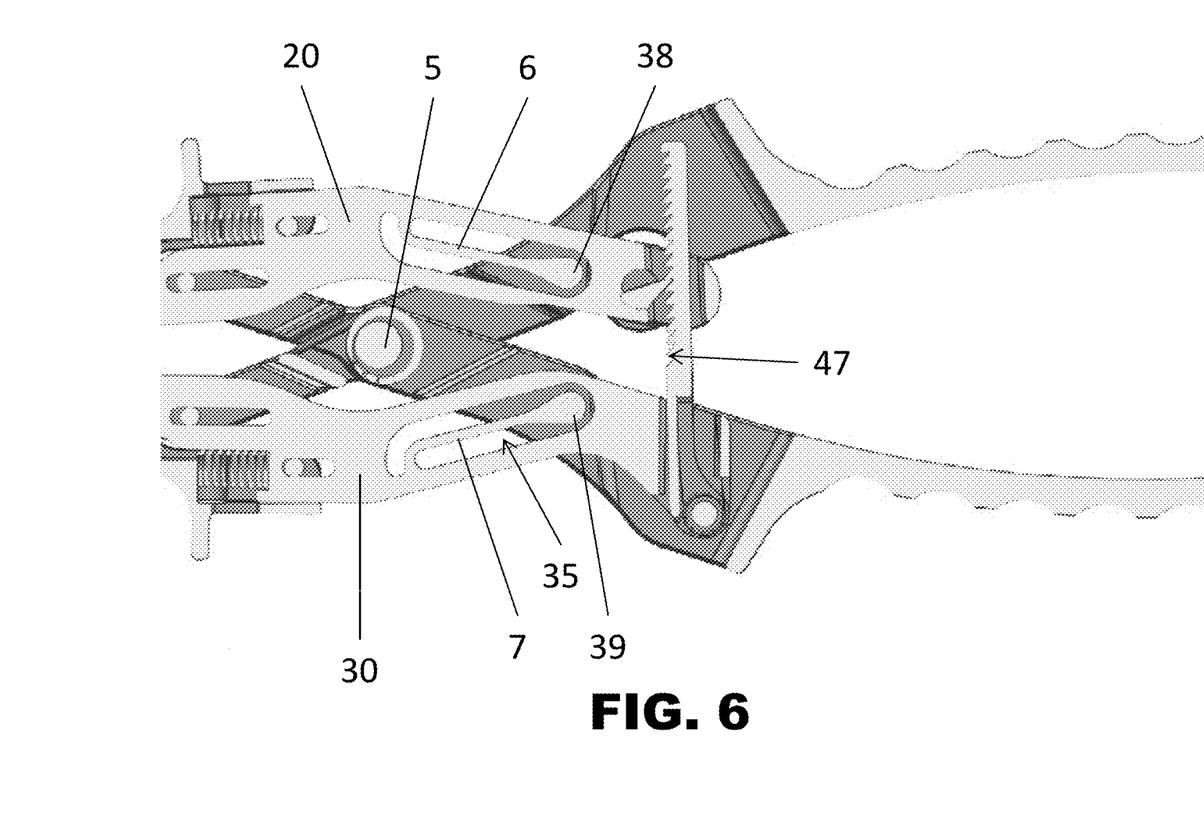
Figure 7:
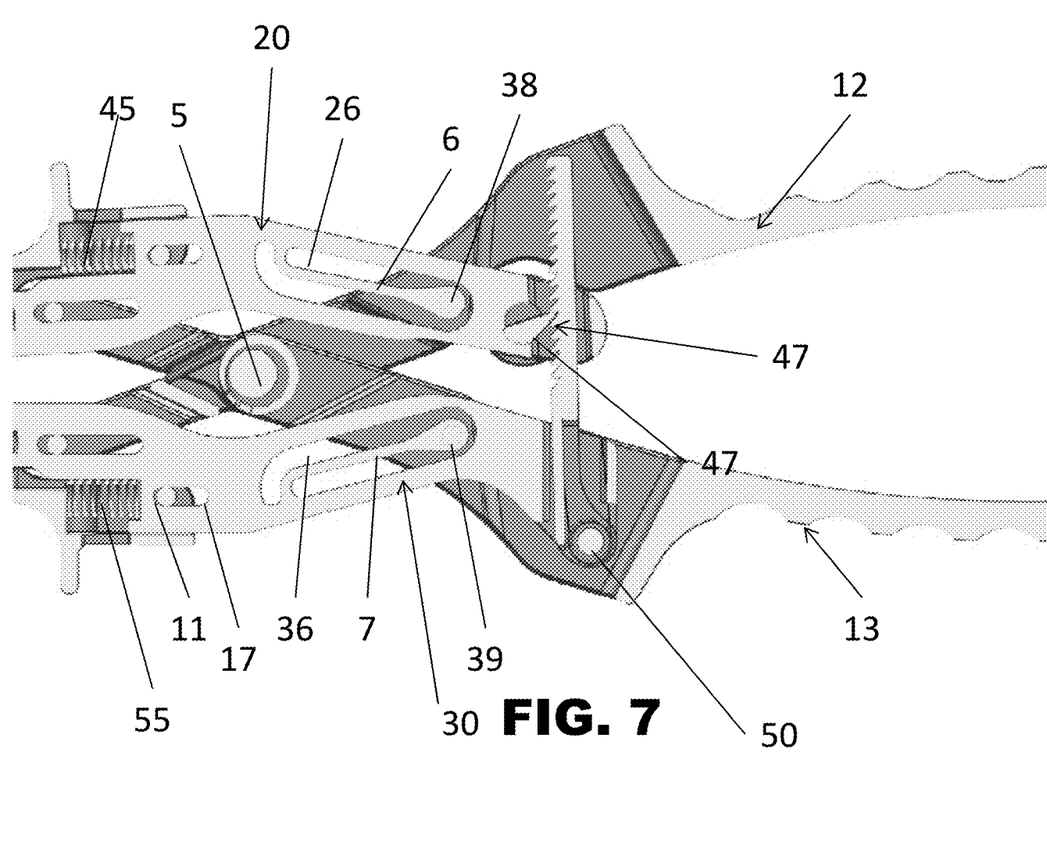
Figure 8:
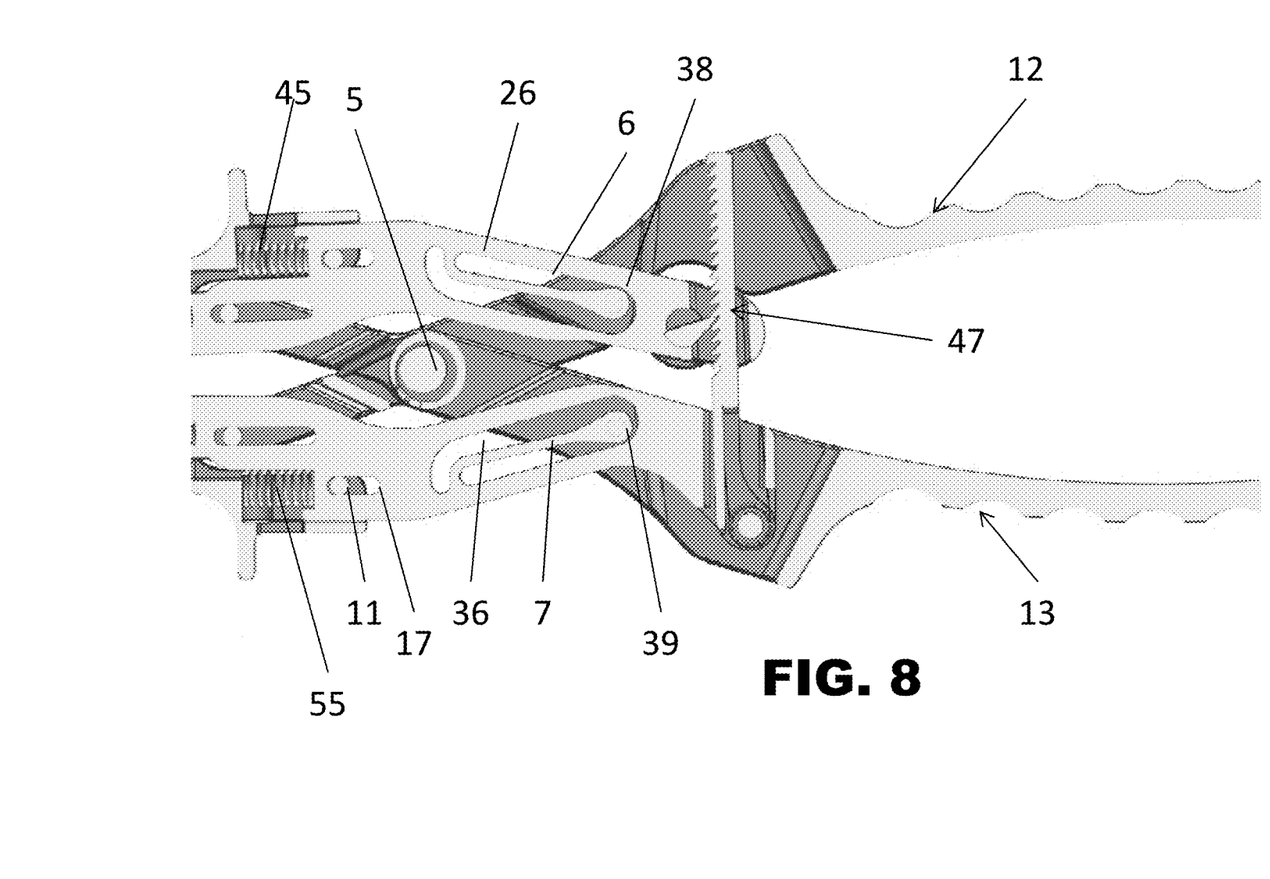
Figure 9:
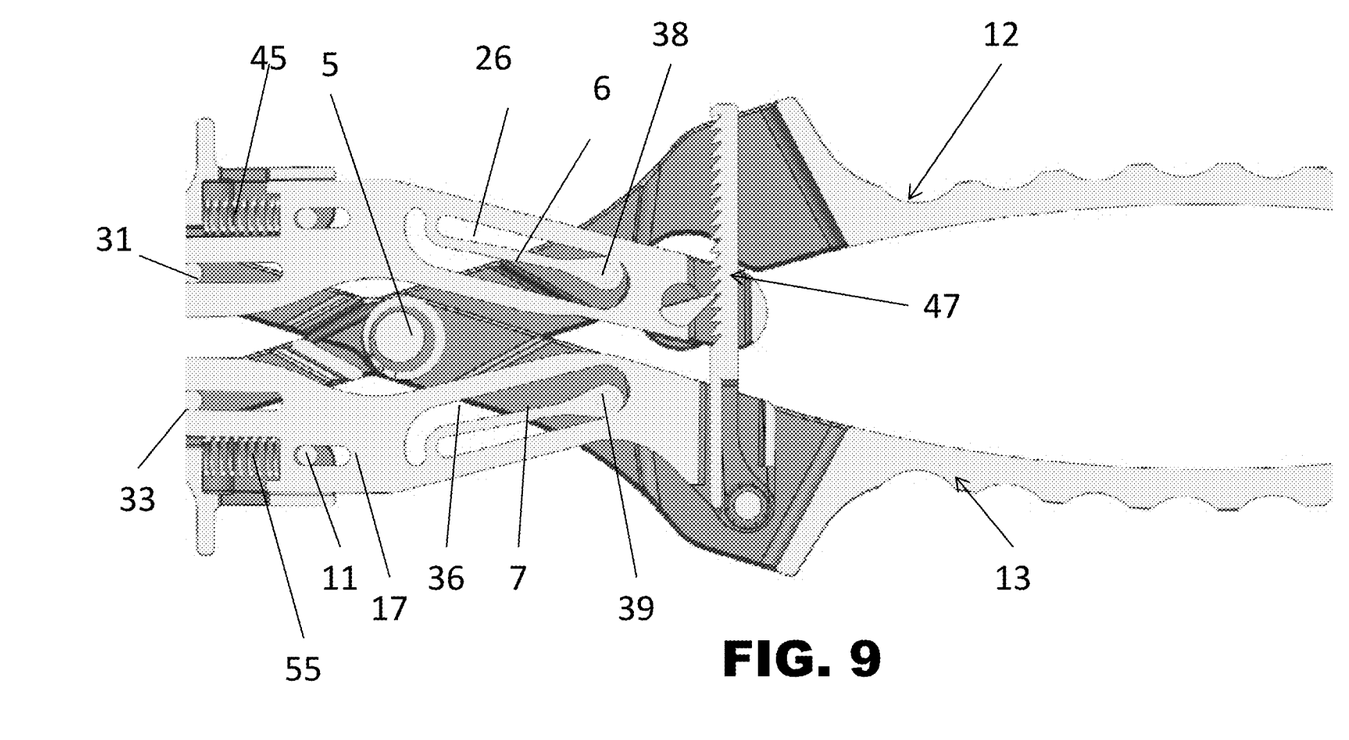
Figure 10:
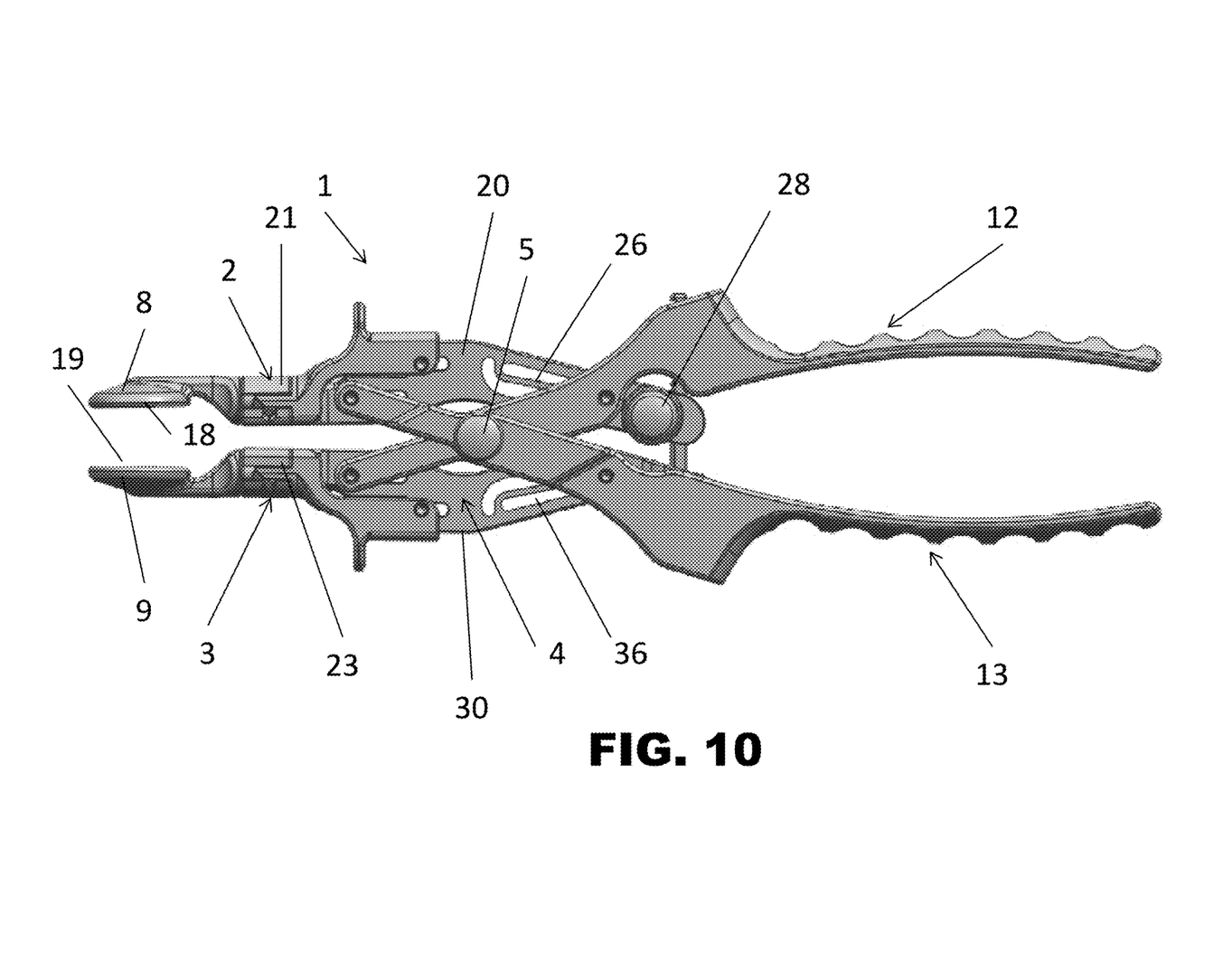
FIG. 10 shows another schematic and top view of an orthopedic surgical pliers-like tool realized according to the present invention in a final position if compared with the position shown in FIG. 1.

As may be appreciated by the examples of the FIGS. 6, 7 and 8, the link between the handle members 12, 13 and the enlarged free ends 38, 39 of the elastic elements 6, 7 moves first of all these elastic elements before they reach a respective internal edge of the openings 26, 36.

Once this the enlarged free ends 38 and 39 have reached the position wherein they abut against the respective internal edge of the openings 26, 36, then the corresponding arms 20, 30 may move and bent to get closer.

This first elastic reaction allows the tool to exert a gripping and holding force that is particularly gentle with respect to the patella bone.

When the distal clamp portions 8, 9 of the jaws 2, 3 have reached a holding position corresponding to the patella bone thickness, that configuration is blocked by the locking means 47.

According to the surgeon needs, the handle members 12, 13 may be closed further applying a further pressure action that will meet the elastic reaction of the compression springs 45, 55 that will allow a further closing and gripping action still under elastic conditions.

By deforming these compression springs, it will be applied a second elastic force on the distal clamp portions 8, 9 of the jaws 2, 3.

In this way, the tooth rack will allow to engage up to other three more teeth of the locking means 47.

By applying this extra force through the handle members 12, 13, the resulting gripping action will be transmitted through the whole instrument up to on the distal clamp portions 8, 9 of the jaws 2, 3 that will pressurize gently the patella bone ensuring a stable gripping. Moreover, when the arms 20, 30 are pre-inclined in the unloaded condition, then the same arms 20, 30 will be nearly parallel to each other in the fully loaded condition to optimize the load transfer to the patella bone.

The tooth rack positioned at the end of the arms 20, 30 is stopping and keeping the desired distance. Pushing the button at the tooth rack will release the tooth and allows the arms/handles to open.

Figure 11:
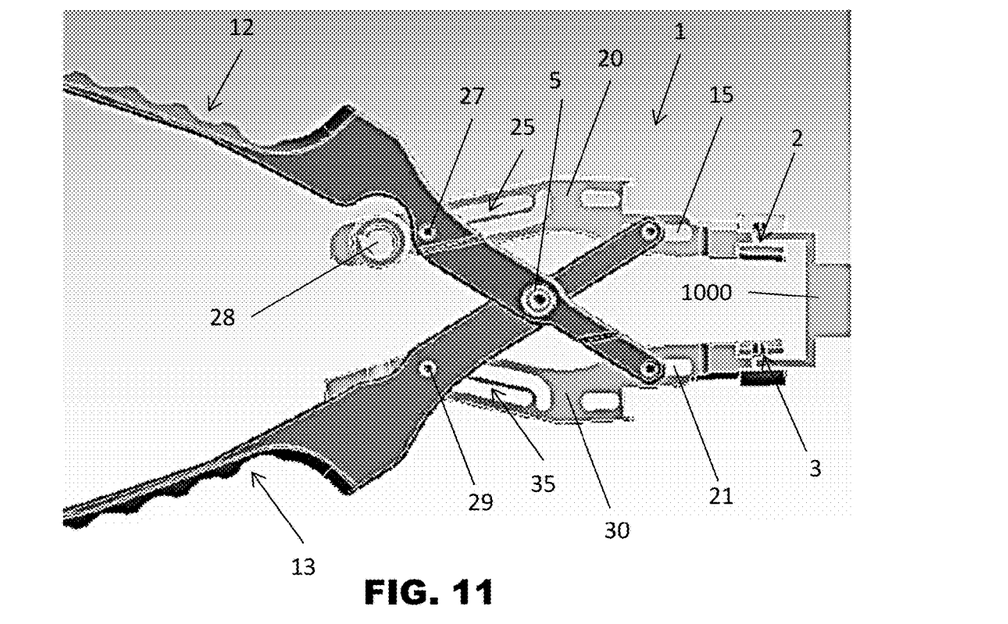
FIG. 11 and FIG. 12 compare a pliers-like tool having elastic members integrated into the arms thereof according to the present invention, with an example of pliers-like tool having no elastic members in the arms thereof.
Figure 12:
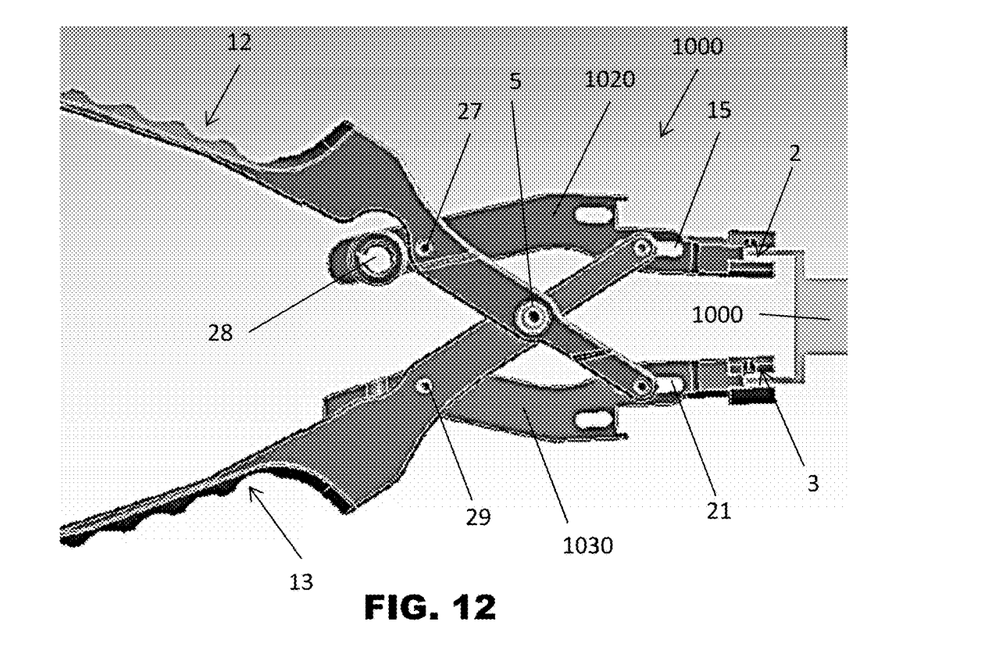

With reference to FIGS. 11 and 12, the effects of the elastic members integrated into the arms of pliers-like tool of the present invention, will be discussed.

Tool 1 of FIG. 11 corresponds to the orthopedic surgical pliers of the present invention, already described above.

Tool 1001 of FIG. 12 is a different example of tool, wherein the arms 1020 and 1030 interposed between the handle members 12, 13 and the jaws 2, 3 are modified. In particular, the arms 1020 and 1030 comprise a bulk body without any elastic member. The arms 1020 and 1030 are thus directly coupled to the handle members 12, 13.

A finite-element (FEM) simulation has been carried out to compare the performances of the tool 1 of FIG. 11 and of the tool 1001 of FIG. 12, also referred to as "patellar pliers" or simply "pliers" in the following.

In operation, the patellar pliers will close without resistance until the attachments (i.e. clamps) will be in contact with the patellar bone. To simulate this contact situation and to facilitate the calculations, in the present example the attachments are replaced by one rigid "phantom body" 1000.

In the example, once the clamps are in contact with body 1000, any further closure of the handle members 12 and 13 will cause a deformation of the arms 20, 30 or 1020, 1030 of the pliers.

In case of tool 1, the elastic members 25 and 35 will mainly absorb the deformation. Differently, in case of tool 1001 the whole arms 1020 and 1030 will deform, according to the elastic properties of a bulk metal material.

Describing more in detail the operation of the tool 1, the upper handle member 12 can only rotate about the center of rotation of hinge bolt 5. A rotational movement will be imposed, and the torque needed for that angular rotation will be calculated. The same is valid also for the lower handle member 13.

The upper arm 20 is connected to the upper handle member 12 by pin 27, and is further connected to the lower handle member 13 by the slot 15, which allows a sliding of pin 31.

The lower arm 30 is connected to the lower handle member 13 by pin 29, and is further connected to the upper handle member 12 by the slot 21, which allows sliding of pin 33.

Applying both rotations in opposite direction on both handle members 12 and 13, both arms 20, 30 or 1020, 1030 will close.

This closing movement will lead to a vertical (downward) movement of the saw-toothed bar 49 and at the same time a vertical (upward) movement of the hinge 50 of the ratchet 47 (directions defined as represented in FIG. 11 and FIG. 12). These movements are estimated considering the position of the pushing button 28 of the ratchet 47.

It is the sum of the movements of both arms 20, 30 or 1020, 1030 that will provide engaging a subsequent tooth of ratchet 47. In the present example the distance between two subsequent teeth, is assumed 2.05 mm.

As a result, the sum of both torques applied on both handle members 12, 13 may be correlated to the sum of the vertical movement of a given tooth and of the tooth rack in ratchet 47.

The resulting torque will be normalized to a distance of interest, equal to the assumed distance between two subsequent teeth of 2.05 mm.

The simulation is calculated for elastic deformation (i.e. no plastic deformation). In the elastic range, a linear correlation between torque and movement can be assumed.

For a better comparison of the performances of tool 1 and tool 1001, the force needed to achieve the necessary torque, will be calculated by considering a single point of application (representing a user's hand in the thumb-index region) at the initial part of the grip of handle members 12 and 13, being 120 mm from the center of rotation of hinge 5.

By carrying out a FEM simulation for tool 1 of FIG. 11, the following is calculated:
Torque on upper handle: 13448 N·mm
Torque on lower handle: 13037 N·mm
Total torque: 26485 N·mm
Horizontal movement of upper arm: −2.757 mm (downward)
Horizontal movement of lower arm: 2.997 mm (upward)
Total movement: 5.754 mm In case of tool 1, a torque of 26485 N·mm will provide closing of the two handle members 12, 13 of about 5.754 mm.

Normalized to one step of the tooth rack, the normalized torque is: (2.050/5.745*26485)=9436 N·mm.

For a lever of 120 mm, this corresponds to normalized force of (9436/120)=79 N applied in the application point, for tool 1.

Considering now an analogous FEM simulation for tool 1001 of FIG. 12, the following is calculated:
Torque on upper handle: 88411 N·mm
Torque on lower handle: 88341 N·mm
Total torque: 176752 N·mm
Horizontal movement of upper arm: −0.903 mm (downward)
Horizontal movement of lower arm: 0.861 mm (upward)
Total movement: 1.764 mm In case of tool 1001, a torque of 176752 N·mm will provide closing of the two handle members 12, 13 of about 1.764 mm.

Again, normalized to one step of the tooth rack, the normalized torque is: (2.050/1.764*176752)=205409 N·mm.

For a lever of 120 mm, this corresponds to normalized force of (205409/120)=1712 N applied in the application point, for tool 1001.

According to the FEM simulation, for a normalized distance of 2.05 mm, tool 1 would require a closing force of 79 N, while tool 1001 would require a force of 1712 N (which is 21.8 times the latter).

The elastic members 25, 35 which are integrated into the arms 20, 30 reduce (of about 22 times) the required force, which is needed to close the ratchet 47 of one tooth, compared to the situation in the arms 1020 and 1030, not having elastic members.

The force required by tool 1 (calculated as 79 N) is easily achievable by one hand only of a user, whereas the force required by tool 1001 (calculated as 1712 N) is not easily achievable by the user.

The skilled in the art appreciates that analogous considerations can be made for clamping of a patellar bone, instead of a rigid body.

The force on the attachments, clamping the patellar bone, would be reduced by the same factor, in tool 1 according to the present invention.

Therefore, with the orthopedic surgical pliers-like tool of the present invention, a gentle clamping of the patellar bone is possible without destroying the delicate bone.

In understanding the scope of the present invention, the term "comprising" and its derivatives, as used herein, are intended to be open ended terms that specify the presence of the stated features, elements, components, groups, integers and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts unless otherwise stated.

Also, it will be understood that although the terms "first" and "second" may be used herein to describe various components these components should not be limited by these terms. These terms are only used to distinguish one component from another.

While only selected embodiments have been chosen to illustrate the present invention, it will be apparent to those skilled in the art from this disclosure that various changes and modifications can be made herein without departing from the scope of the invention as defined in the appended claims.

What is claimed is:

1. Orthopedic surgical pliers-like tool for performing surgery on a patella bone comprising:
at least a couple of jaws coupled to handle members pivotally mounted with a hinge bolt in relation with one another;
each jaw having a distal clamp portion for gripping and holding at least a periphery of a patella bone;
an intermediate force transmission mechanism between the handle members and the jaws coupled to the hinge bolt;
said intermediate force transmission mechanism comprising a couple of arms positioned around the hinge bolt and structurally independent from the handle members and interposed between the handle members and the jaws;
each arm comprising an elastic member formed therein coupling each arm to a corresponding handle member, of the handle members, at a proximate portion of the handle member at a first linking point defined by the elastic member;
a second, more distal, linking point in each arm engaging a distal end of a handle member of the handle members;
the first linking point of one arm and the second linking point of the other arm being cross linked to a same handle member of the handle members.

2. The pliers-like tool according to claim 1, characterized in that said arms are structured to be not parallel in an unloaded condition and to be kept substantially parallel to each other in a fully loaded condition.

3. The pliers-like tool according to claim 1, wherein each of said arms is substantially flat and has an arched shape with the distal end coupled to a corresponding jaw and a proximal end overlapping the handle members more proximally with reference to the hinge bolt.

4. The pliers-like tool according to claim 1, wherein each elastic member comprises an opening in one corresponding arm, wherein an elastic element or tongue is protruding inside the opening.

5. The pliers-like tool according to claim 1, wherein each elastic member comprises an opening in one corresponding arm, wherein the elastic member includes a leaf spring which is provided having one end fixed to the arm structure and other end free to move inside a respective opening of the elastic member.

6. The pliers-like tool according to claim 4, wherein the elastic element has an enlarged free end linked to the first linking point of the corresponding handle member, of the handle members, by a corresponding pin.

7. The pliers-like tool according to claim 1, wherein said second more distal linking point is located in a slot formed in each of the arms and engaged by a corresponding sliding pin fixed perpendicularly to the distal end of each handle member.

8. The pliers-like tool according to claim 6, wherein each handle member is cross linked to said enlarged free end of the elastic element of one arm by a pin located in an intermediate position of the handle member and to the other arm by a sliding pin located at the distal end of the handle member and sliding inside a slot of the other arm.

9. The pliers-like tool according to claim 8, wherein said sliding pin is fixed perpendicularly to the distal end of each handle member.

10. The pliers-like tool according to claim 1, wherein each jaw of said couple of jaws is mounted in a removable manner on the distal end with an elastic element.

11. The pliers-like tool according to claim 10, wherein a guide slot is provided at the distal end of each arm comprising a corresponding pin formed integrally connected with a corresponding jaw and extended in a direction perpendicular to a longitudinal extension of the couple of jaws.

12. The pliers-like tool according to claim 11, wherein each of said pins is free to slide inside the guide slot to provide an axial movement of each jaw on the respective arm relative to an elastic element.

13. The pliers-like tool according to claim 1, wherein a locking means is provided at proximal ends of the arms, to maintain a desired distance between the distal clamp portions of the jaws.

14. The pliers-like tool according to claim 13, wherein said locking means includes a saw-toothed bar that is pivotally mounted on a hinge at a proximal end of one arm and is engaged by a ratchet provided on the proximal end of the other arm when the arms are forced to approach one toward the other by the handle members.

15. The pliers-like tool according to claim 14, wherein a pushing button is provided on the proximal end of one arm to release the ratchet from its engagement with teeth of the saw-toothed bar and release the handle members for returning the tool in the ready to use position.

16. The pliers-like tool according to claim 1, wherein a compression spring is provided between an arm of the arms and a jaw of the couple of jaws.

17. The pliers-like tool according to claim 1, wherein the distal clamp portions of the jaws are removable and are supported by a corresponding pin that is supported in a seat provided at the distal end of each of said arms; a fastener mechanism being provided on each of the jaws to release said distal clamp portions.

18. The pliers-like tool according to claim 4, wherein the elastic element has an enlarged free end linked to a first link point of the handle member by a corresponding pin.

19. The pliers-like tool according to claim 18, wherein each handle member is cross linked to said enlarged free end of the elastic element of one arm by a pin located in an intermediate position of the handle member and to the other arm by a sliding pin located at the distal end of the handle member and sliding inside a slot of the other arm.

20. The pliers-like tool according to claim 19, wherein said sliding pin is fixed perpendicularly to the distal end of each handle member.

* * * * *